US009976417B2

(12) United States Patent
Mahavadi et al.

(10) Patent No.: US 9,976,417 B2
(45) Date of Patent: May 22, 2018

(54) CAPILLARY ELECTROPHORESIS FOR RESERVOIR FLUID ANALYSIS AT WELLSITE AND LABORATORY

(71) Applicant: Schlumberger Technology Corporation, Sugar Land, TX (US)

(72) Inventors: Sharath Chandra Mahavadi, Edmonton (CA); Geza Horvath Szabo, Sugar Land, TX (US); Simon Ivar Andersen, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 81 days.

(21) Appl. No.: 14/398,961

(22) PCT Filed: Jun. 13, 2013

(86) PCT No.: PCT/US2013/045589
§ 371 (c)(1),
(2) Date: Nov. 4, 2014

(87) PCT Pub. No.: WO2014/014587
PCT Pub. Date: Jan. 23, 2014

(65) Prior Publication Data
US 2015/0114837 A1 Apr. 30, 2015

Related U.S. Application Data

(60) Provisional application No. 61/672,075, filed on Jul. 16, 2012.

(51) Int. Cl.
*G01N 27/447* (2006.01)
*E21B 49/08* (2006.01)
*G01N 30/88* (2006.01)

(52) U.S. Cl.
CPC ............ *E21B 49/08* (2013.01); *E21B 49/081* (2013.01); *G01N 27/44704* (2013.01);
(Continued)

(58) Field of Classification Search
CPC ...................... G01N 27/447–27/44795; B01D 57/00–57/02; C92F 1/4696
(Continued)

(56) References Cited

U.S. PATENT DOCUMENTS 5,141,621 A    8/1992  Zare et al.
5,269,901 A    12/1993 Dill et al.
(Continued)

FOREIGN PATENT DOCUMENTS

EP    0339780       8/1996
EP    1909099 A1    4/2008
(Continued)

OTHER PUBLICATIONS

Stella Rovio, Kimmo Sirén, Heli Sirén, "Application of capillary electrophoresis to determine metal cations, anions, organic acids, and carbohydrates in some Pinot Noir red wines," Food Chemistry 2011 vol. 124, Issue 3, pp. 1194-1200.
(Continued)

*Primary Examiner* — Bach T Dinh

(57) ABSTRACT

A method improves the capability for testing a fluid sample, e.g. testing a reservoir sample of hydrocarbon fluid. The methodology comprises positioning a capillary electrophoresis system within an enclosed chamber system. The enclosed chamber system preserves the desired downhole reservoir conditions during testing of the reservoir sample. In some applications, the reservoir sample is divided into a plurality of capillaries of the capillary electrophoresis system to enable testing of the reservoir sample with different types of detectors in one capillary electrophoresis system.
(Continued)

The method can also be applied to depressurized reservoir samples.

25 Claims, 6 Drawing Sheets

(52) U.S. Cl.
CPC . *G01N 27/44717* (2013.01); *G01N 27/44782* (2013.01); *G01N 27/44791* (2013.01); *G01N 2030/8854* (2013.01)

(58) Field of Classification Search
USPC ............... 204/450–470, 546–550, 600–621, 204/643–645
See application file for complete search history.

(56) References Cited

U.S. PATENT DOCUMENTS

| | | | |
|---|---|---|---|
| 5,297,420 A | 3/1994 | Gilliland et al. | |
| 5,312,535 A | 5/1994 | Waska et al. | |
| 5,584,982 A * | 12/1996 | Dovichi ........... | G01N 27/44721 204/452 |
| 5,667,657 A | 9/1997 | Recknor et al. | |
| 5,675,155 A | 10/1997 | Pentoney, Jr. et al. | |
| 5,885,430 A | 3/1999 | Kernan et al. | |
| 5,916,428 A | 6/1999 | Kane et al. | |
| 5,972,187 A | 10/1999 | Parce et al. | |
| 6,531,041 B1 * | 3/2003 | Cong ............... | G01N 27/44721 204/452 |
| 6,939,717 B2 | 9/2005 | Jiang et al. | |
| 7,231,819 B2 | 6/2007 | Jones et al. | |
| 7,364,705 B2 | 4/2008 | Sundberg et al. | |
| 7,381,317 B2 | 6/2008 | Liu et al. | |
| 7,857,955 B2 | 12/2010 | Ratnayake et al. | |
| 8,340,913 B2 | 12/2012 | Mostowfi et al. | |
| 8,485,026 B2 | 7/2013 | Mostowfi | |
| 8,881,577 B1 | 11/2014 | Agar et al. | |
| 2002/0179532 A1 * | 12/2002 | Citterio ............ | G01N 27/44752 210/656 |
| 2003/0000838 A1 * | 1/2003 | Yeung .................... | B01D 15/34 204/603 |
| 2003/0013147 A1 | 1/2003 | Hildenbrand | |
| 2003/0052008 A1 | 3/2003 | Liu et al. | |
| 2003/0116436 A1 * | 6/2003 | Amirkhanian ... | G01N 27/44721 204/452 |
| 2003/0116438 A1 * | 6/2003 | Yamazaki ........ | G01N 27/44708 204/601 |
| 2003/0196896 A1 | 10/2003 | McWaid et al. | |
| 2004/0045350 A1 | 3/2004 | Jones et al. | |
| 2007/0111329 A1 | 5/2007 | Guzman | |
| 2009/0159288 A1 | 6/2009 | Szabo et al. | |
| 2009/0294175 A1 | 12/2009 | Cartellieri | |
| 2015/0114837 A1 | 4/2015 | Mahavadi et al. | |

FOREIGN PATENT DOCUMENTS

| | | |
|---|---|---|
| WO | 95/10344 A1 | 4/1995 |
| WO | 01063094 A1 | 8/2001 |
| WO | 01/73424 A1 | 10/2001 |
| WO | 0198630 A1 | 12/2001 |
| WO | 02059589 A2 | 8/2002 |
| WO | 03010528 A1 | 2/2003 |
| WO | 2013062879 A1 | 5/2013 |

OTHER PUBLICATIONS

Norman J. Dovichi, "DNA sequencing by capillary electrophoresis," Electrophoresis vol. 18 Issue 12-13, 1997, pp. 2393-2399.
W.T. Kok, A.J. Tudo, M. Grutters, A.G. Shepherd, "Characterization of Asphaltenes by Nonaqueous Capillary Electrophoresis," Energy & Fuels 2011 vol. 25 Issue 1, pp. 206-214.
"Blue4Green" at http://www.blue4green.com/.
European Search Report for corresponding EP Application Serial No. 13819418.8, dated Jan. 30, 2017, 6 pages.
International Preliminary Report on Patentability issued in the related PCT application PCT/US2014/051208, dated Feb. 16, 2016 (7 pages).
Examination Report received in the related GC Application GC/2013/24951, dated Nov. 20, 2016 (5 pages).
Office Action issued in the EP Application 13819418.8, dated Mar. 15, 2017 (11 pages).
International Search Report and the Written Opinion for International Application No. PCT/US2014/051208 dated Dec. 23, 2014.
M.I. Al-Katheeri and H.A. Nasr-El-Din, SPE, Saudi Aramco, "Application of CE and CE-MS to Assay Corrosion Inhibitors Used in Well-Stimulation Treatments," SPE 95112, SPE International Symposium on Oilfield Corrosion held in Aberdeen, United Kingdom, May 13, 2005.

* cited by examiner

CAPILLARY ELECTROPHORESIS FOR RESERVOIR FLUID ANALYSIS AT WELLSITE AND LABORATORY

BACKGROUND

Hydrocarbon fluids, e.g. crude oil, contain different organic moieties with diverse functionalities including asphaltenes, saturates, aromatics, long and short chain organic acids, amines, and/or others. Injection water or produced water related to oil production contains both ions and organic substances. Analyzing reservoir-related fluids provides insight with respect to potential problems related to a hydrocarbon fluid reservoir. Data from the analysis can be useful in understanding the quality and economic value of produced fluids from the reservoir and can guide production strategy. Depending on the application, analysis to help understand the composition of hydrocarbon fluid and/or water produced or injected may be used to enable improved control over the production and/or injection operation. The fluids may be analyzed at the wellhead or in a laboratory, although the results of surface-based analyses may be compromised due to the very different conditions between the surface and the subterranean location.

SUMMARY

In general, the present disclosure provides a method for testing a reservoir sample, e.g. testing a sample of hydrocarbon fluid. The methodology comprises positioning a capillary electrophoresis system within an enclosed chamber system. The enclosed chamber system facilitates preserving the desired downhole reservoir conditions during testing of the reservoir sample. In some applications, the reservoir sample is divided into a plurality of capillaries of the capillary electrophoresis system to enable testing of the reservoir sample with a plurality of different types of detectors in a single capillary electrophoresis system. Alternatively, multiple reservoir sample types may be tested with a single detector.

However, many modifications are possible without materially departing from the teachings of this disclosure. Accordingly, such modifications are intended to be included within the scope of this disclosure as defined in the claims.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

Figure 1:
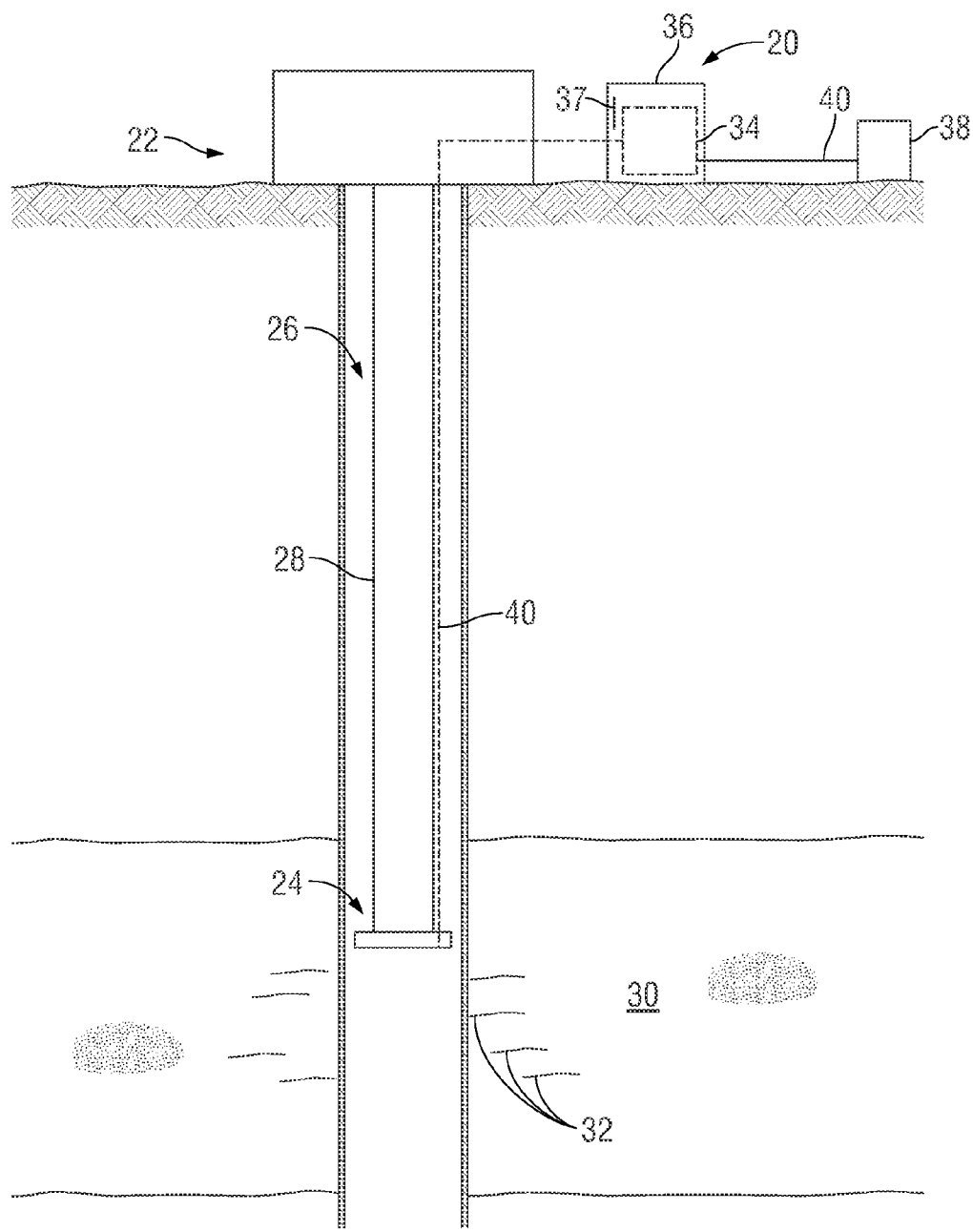
FIG. 1 is a schematic illustration of an example of a well system and a capillary electrophoresis system for analyzing a sample of reservoir fluid, according to an embodiment of the disclosure.

In the following description numerous details are set forth to provide an understanding of some embodiments of the present disclosure. However, it will be understood by those of ordinary skill in the art that the system and/or methodology may be practiced without these details and that numerous variations or modifications from the described embodiments may be possible.

The present disclosure generally relates to a methodology for improved testing of fluids, e.g. hydrocarbon or aqueous fluids, obtained from a subterranean environment. For example, a fluid sample may be obtained from a hydrocarbon reservoir, such as a crude oil/natural gas reservoir, and the present methodology enables analysis of the reservoir sample at a very early stage. The methodology also enables gathering of a variety of data on the reservoir sample to help understand the quality, and thus the economic value, of the fluids produced from the reservoir. In some applications, the quality of water produced or injected also is analyzed to improve controls in flow assurance and reservoir management. Growth in the shale gas industry, unconventional crude oil and gas production, carbon dioxide sequestration, and carbon dioxide storage in deep aquifers, encourage the use of water testing, and the present methodology facilitates such testing.

As described in greater detail below, an embodiment of the methodology employs a capillary electrophoresis system. A fluid sample is obtained from the reservoir and analyzed at an early stage via the capillary electrophoresis system. The capillary electrophoresis system may be pressure and/or temperature controlled to ensure improved analysis of the fluid sample under desired reservoir conditions. Additionally, the capillary electrophoresis system may be a multi-capillary system with a variety of detectors which operate under different principles to obtain different datasets for expanded analysis of the fluid sample in a single capillary electrophoresis system.

Operating the capillary electrophoresis system at an early stage and under at least some of the reservoir conditions enables accurate testing while avoiding pressure changes that can lead to gas separation. Such pressure changes and gas separation can affect the pH value of the sample and lead to precipitation or deposition of sample constituents. Similarly, testing under reservoir conditions also may be employed to avoid temperature changes that can further lead to precipitation. When such phase separation processes occur, a portion of the dissolved ions of the sample may not reach the sampling point and the total composition of such incorrectly sampled fluid becomes tainted.

Employing the capillary electrophoresis system at a wellsite or in a commercial laboratory can be very helpful because capillary electrophoresis can be used to separate, detect, and quantify all types of ions, including metal ions, in a relatively short time. A wellsite capillary electrophoresis methodology for analyzing fluids at reservoir conditions, and a capillary electrophoresis system for laboratory and wellsite sample analysis under ambient conditions is described in greater detail below. Capillary electrophoresis is useful in detecting many types of organic and inorganic ions in aqueous and organic samples.

When conditions limit the ability to measure and analyze fluid samples downhole, the present methodology facilitates early analysis of fluid samples at created reservoir conditions. According to an example, a capillary electrophoresis system cooperates with or comprises a robust, enclosed chamber system to enable testing of a variety of fluids under reservoir conditions. The testing may be conducted at the wellsite or in a laboratory on a variety of reservoir fluids, such as oil, gas and/or water, soon after the reservoir sample is obtained. For example, the testing may be performed in conjunction with a variety of oilfield applications, including well monitoring and testing applications related to monitoring and testing injected and produced water composition in enhanced oil recovery (EOR) applications and testing of production fluids from shale reservoirs. Additionally, the capillary electrophoresis system may be used for testing and monitoring fluids stored in deep aquifers. In one example, the capillary electrophoresis system may be used to monitor carbon dioxide sequestration. However, the system and testing methodology may also be used to monitor fluid composition of fluid samples taken from many subterranean environments and applications. In well-related and non-well-related applications, the more accurate monitoring of fluids is useful in preventing or reducing downtime with respect to reservoirs and/or production plants.

Although the overall fluid sample testing system may be constructed in various configurations, an example utilizes a capillary electrophoresis system employing a silica capillary (with or without internal coating) located in a tubing of high mechanical strength, e.g. a metal tubing. The tubing contains inlet and outlet ports for enabling flow of coolant fluid along the capillary and for thus avoiding temperature gradients from the walls of the capillary to the center of the capillary. In some applications, multiple capillaries are provided in parallel to carry out different types of tests or multiple test runs in a single operation. The capillaries may be designed with narrow bores which encourage rapid heat dissipation. The capillaries also may be formed as flexible capillaries with sufficient flexibility to withstand physical shocks incurred during, for example, deployment to and operation at the downhole location. Additionally, the outer metal tubing may contain a connection point through which information, e.g. test data, from the capillaries may be transmitted to, for example, a data acquisition and control system.

The capillary electrophoresis system may be designed for independent operation or for cooperation with other systems. Additionally, the capillary electrophoresis system may comprise a variety of detectors which operate based on different principles and techniques, including emission or absorption optical techniques or electromagnetic spectroscopic techniques. The detectors also may comprise electrochemical detectors based on conductivity or resistance and/or potentiometric detectors. In some applications, single or multiple capillaries are placed inside microchip channel devices for heat exchange and/or detection. Thus the methodology enables dividing the reservoir sample into multiple capillaries and then testing and analyzing the fluid in the various capillaries with different types of detectors and/or separating organic and aqueous phases in a reservoir sample and analyzing them simultaneously in different capillaries with similar detectors.

Depending on the specifics of a given application, the testing methodology may be employed for testing a variety of fluids. In many applications, the testing methodology may be used to detect and monitor specific ions or groups of ions. For example, the methodology may be applied downhole to detect common ions in the aqueous reservoir fluids which are not limited to cations viz., $Li^+$, $Na^+$, $K^+$, $Mg^{2+}$, $Ca^{2+}$, $Sr^{2+}$, $Ba^{2+}$, $NH_3^+$, $Fe^{2+}$, $Fe^{3+}$; anions viz., F, $Cl^-$, $Br^-$, $I^-$, $NO_3^-$, $SO_4^{2-}$, $CO_3^{2-}$, $BO_3^{3-}$, and $PO_4^{3-}$, inorganic and organic mercury ions ($Hg^{2+}$, $Hg^+$, R—Hg; R=$CH_3$—$(CH_2)_n$, R=0, 1, . . . n), organic acids not limited to naphthenic acids and organic amines.

Referring generally to FIG. 1, an embodiment of a well system for obtaining samples and a testing system is illustrated. For example, the well system may be employed in a wellbore and utilized for obtaining reservoir samples from a subterranean location. The testing system comprises a capillary electrophoresis system having multiple capillaries enclosed by a chamber designed to ensure problem-free operation of the pressure sensitive capillary electrophoresis instrument under re-created reservoir conditions, such as high pressure and high temperature conditions.

In the example illustrated in FIG. 1, a fluid testing system 20, e.g. a capillary electrophoresis system, is designed to re-create reservoir conditions while deployed at a surface location 22, such as at a wellsite or easily accessible laboratory. Depending on the application, the reservoir sample or other fluid sample may be obtained via a variety of well systems 24 deployed to a subterranean location along, for example, a wellbore 26 via a suitable conveyance 28. Conveyance 28 may comprise tubing, cable, wireline, slick line, or another suitable conveyance deployed from surface location 22, e.g. a land surface or a sea surface. In the illustrated application, the fluid sample is a reservoir sample obtained from a reservoir 30 at a subterranean formation. Fluid testing system 20 enables testing and/or monitoring of a well fluid or well fluids 32 located in the subterranean formation 30 by re-creating desired reservoir conditions in a manner which avoids undesirable phase separation processes prior to analysis of the sample, or in case high pressure sampling is not possible at the wellsite the system allows for immediate analysis at ambient or low pressure to avoid compromising the sample by transporting it to an external and distant laboratory. However, fluid testing system 20 may be used for testing and/or monitoring of a variety of other types of fluids obtained from many other types of harsh, high temperature and/or high pressure environments, such as other subterranean environments.

In the embodiment illustrated, fluid testing system 20 comprises a capillary electrophoresis system 34 which is combined with or comprises a chamber system 36 enclosing at least a portion of the capillary electrophoresis system 34. By way of example, the chamber system 36 may comprise a high pressure chamber system which enables control over the pressure to which the capillary electrophoresis system 34 is subjected. The chamber system 36 also may be designed to facilitate temperature control with respect to the capillary electrophoresis system 34. The pressure and/or temperature is controlled by a pressure/temperature controller 37 which may include a pressure source, heater, and/or cooler. In some applications, the capillary electrophoresis system 34 may be designed to cooperate with a data acquisition and control system 38 by outputting (and/or receiving) signals with respect to the data acquisition and control system 38. As illustrated, the data acquisition and control system 38 may be coupled with capillary electrophoresis system 34 via a wired or wireless communication line 40. In the example illustrated, data acquisition and control system 38 is located at a surface location proximate or integrated with capillary electrophoresis system 34, however data acquisition and control system 38 may be located at other locations, including remote surface locations, and/or at multiple locations. Data acquisition and control system 38 may be used to receive and analyze data from fluid testing system 20 and/or to provide control signals to fluid testing system 20 for controlling the sample analysis.

Figure 2:
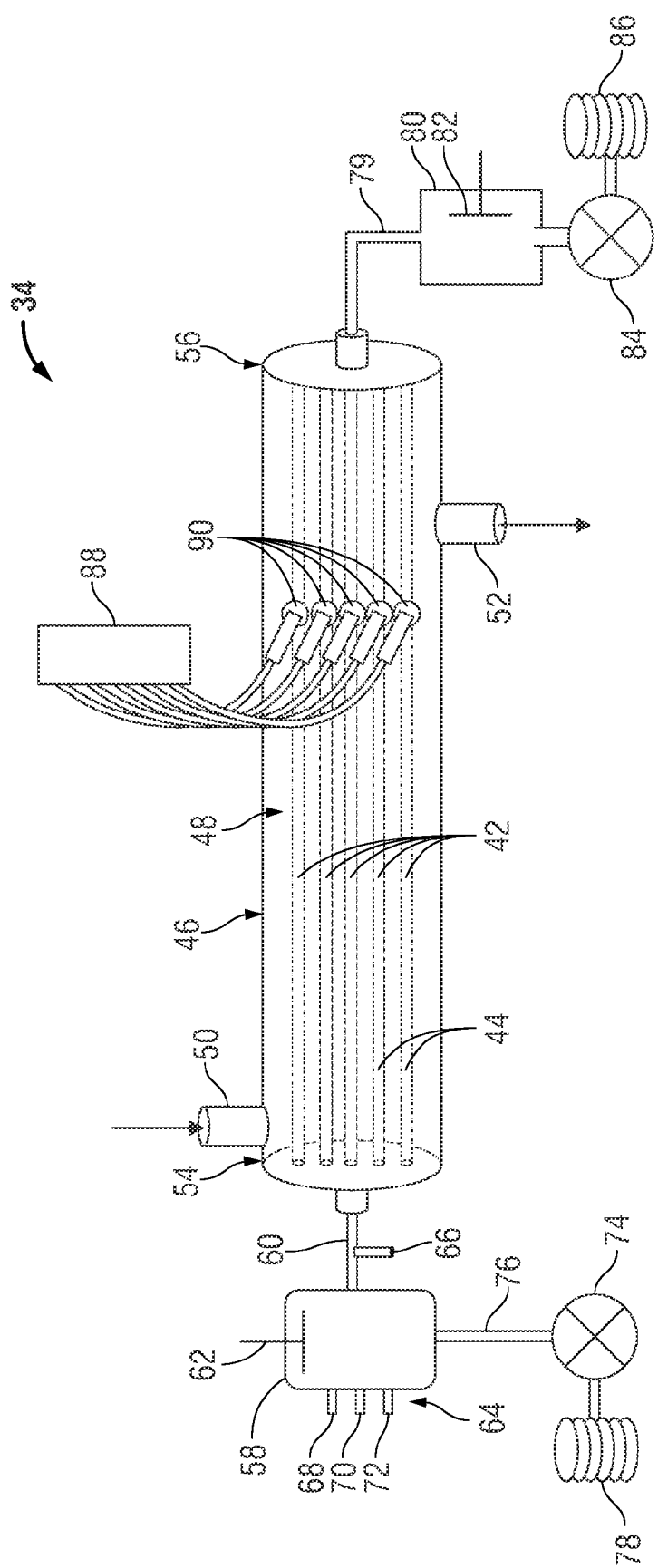
FIG. 2 is a schematic illustration of an example of a capillary electrophoresis system which may be employed to analyze the reservoir sample, according to an embodiment of the disclosure.

Referring generally to FIG. 2, an example of capillary electrophoresis system 34 is illustrated. In this embodiment, capillary electrophoresis system 34 comprises at least one capillary 42 and, in the illustrated embodiment, a plurality of parallel capillaries 42. The capillaries 42 may be formed as flexible capillaries and in some applications they may be coated internally by a suitable coating 44. The plurality of capillaries 42 is disposed within a tubing 46, such as metal tubing designed to protect the capillaries 42 and to provide a flow path for coolant 48. The tubing 46 comprises an inlet 50 and an outlet 52 to accommodate the flow of coolant 48 along the interior of tubing 46 to thus control the temperature along capillaries 42 during testing. For example, coolant 48 may be used to dissipate heat generated while applying a voltage across the capillaries 42 to cause ion and/or molecular separations.

The coolant 48 may be a fluid, e.g. a liquid, having temperature dependent viscoelastic properties. The viscoelastic properties may be designed to improve the shock resistance of the capillaries 42. For example, the coolant 48 may be a high viscosity liquid or an elastic material at lower temperatures and a low viscosity liquid at higher temperatures.

In the embodiment illustrated, the capillaries 42 are coupled to an inlet multivalve port 54 at an inlet end and to an outlet multivalve port 56 at an outlet end. The multivalve ports 54, 56 enable switching of the fluid testing system 20 from one capillary 42 to another. On the inlet side, multivalve port 54 is coupled with an inlet vial 58 via a flow passage 60. A sample supply channel 66 is also coupled to the flow passage 60. The inlet vial 58 may be an anodic chamber having an anode 62 or a microfluidic mixing device. The inlet vial 58 may be supplied with fluids via a plurality of fluid supply channels 64. By way of example, fluid supply channels 64 may comprise a separation buffer fluid supply channel 68, a rinse solution/solvent supply channel 70, and a capillary electrophoresis grade water supply channel 72. As illustrated, inlet vial 58 also is coupled with a pump 74 via a flow passage 76. A waste reservoir 78 may be connected to pump 74 to enable depletion of excess fluid.

On the outlet side, a flow passage 79 connects outlet multivalve port 56 with a fluid vessel 80 having, for example, a cathode 82. In this example, the fluid vessel 80 serves as a cathodic chamber. Through fluid vessel 80, the outlet multivalve port 56 also is connected to a pump 84 and a waste reservoir 86. The pump 84 and the waste reservoir 86 allow flushing and/or rinsing of the capillaries 42 for various applications. As illustrated, the inlet reservoir, e.g. inlet vial 58, and the outlet side waste reservoir 86 are connected to the electrodes, i.e. anode 62 and cathode 82, respectively, to enable electrochemical separation of ions in the sample by applying a voltage across the capillary or capillaries containing the fluid sample.

Figure 3:
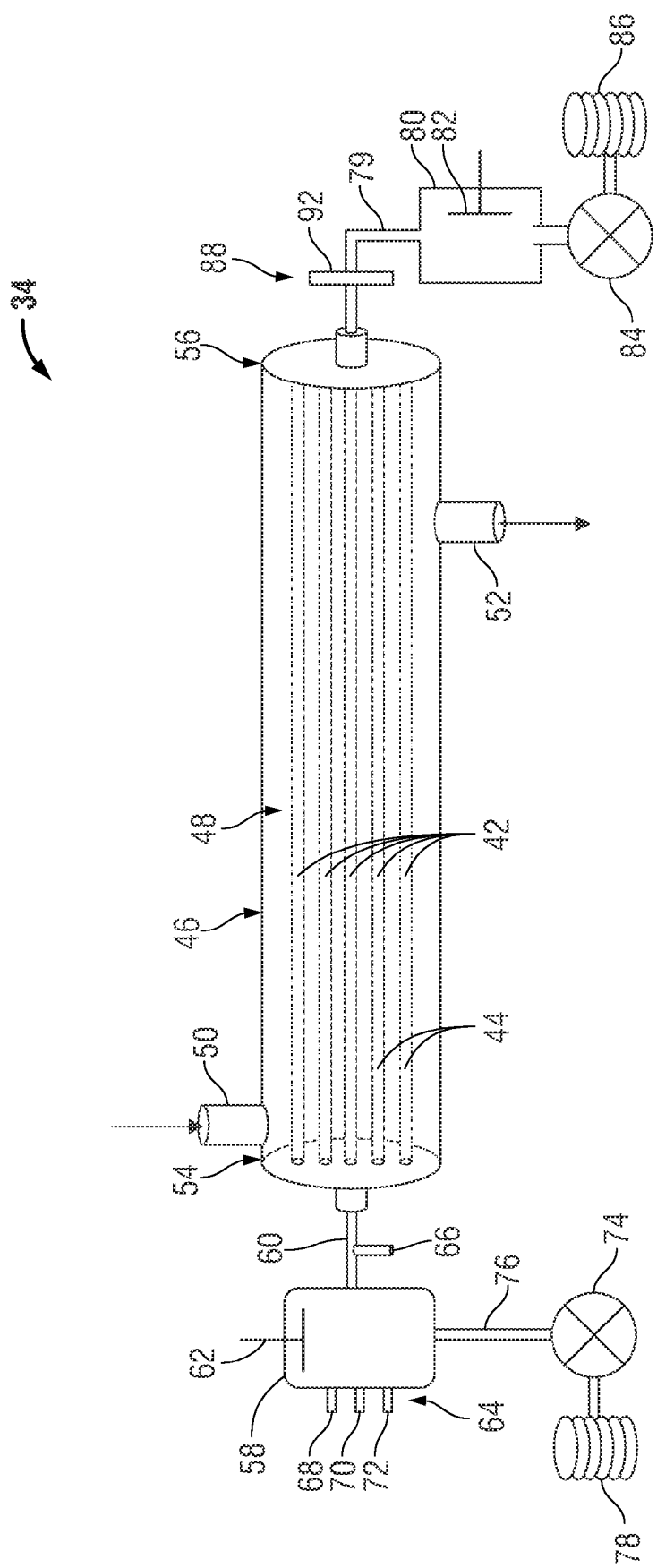
FIG. 3 is a schematic illustration of another example of a capillary electrophoresis system which may be employed to analyze the reservoir sample, according to an embodiment of the disclosure.

A detector system 88 may be employed to detect migrated ions of the sample being tested. By way of example, the detector system 88 may be positioned toward the outlet side of the capillaries 42 for detection of the migrated ions. As illustrated in FIG. 2, the detector system 88 may comprise a plurality of unique detectors/sensors 90 positioned along a plurality of corresponding capillaries 42. The multiple detectors 90 may operate according to different techniques based on different principles to enable detection and analysis of a variety of fluid sample parameters on capillary electrophoresis system 34. By way of example, the detectors 90 may comprise emission or absorption optical detectors, electromagnetic spectroscopic detectors, electrochemical detectors based on conductivity or resistance, potentiometric detectors, and/or a variety of other types of detectors for gathering a wide variety of data on the fluid sample, e.g. reservoir sample. In another embodiment, the detector system 88 may comprise a single sensor 92 positioned along flow passage 79, as illustrated in the embodiment of FIG. 3. The single sensor 92 also may be designed to collect a variety of data that may be analyzed according to different principles or techniques.

Figure 4:
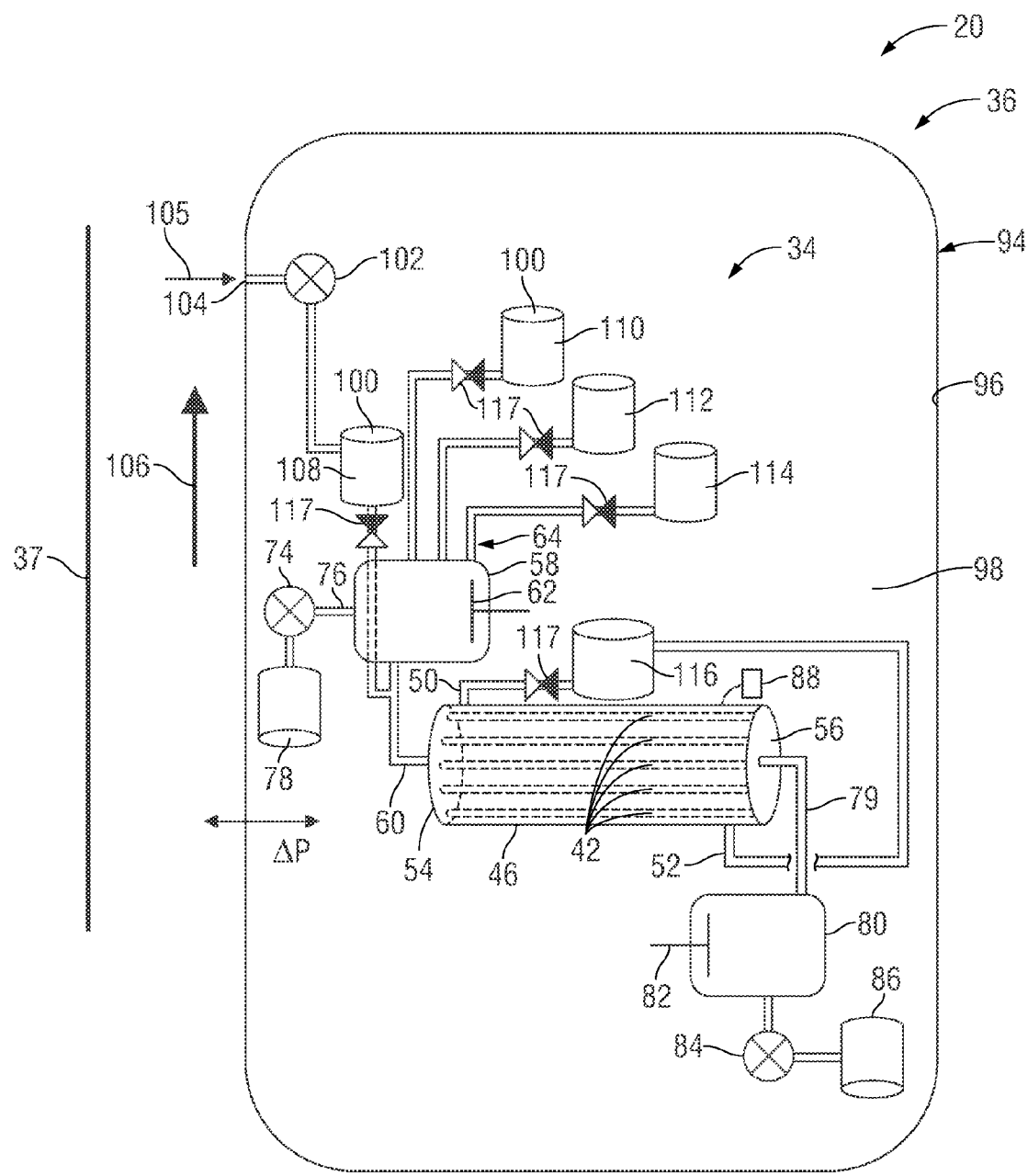
FIG. 4 is a schematic illustration of a capillary electrophoresis system positioned in an embodiment of an enclosed chamber system, according to an embodiment of the disclosure.
Figure 5:
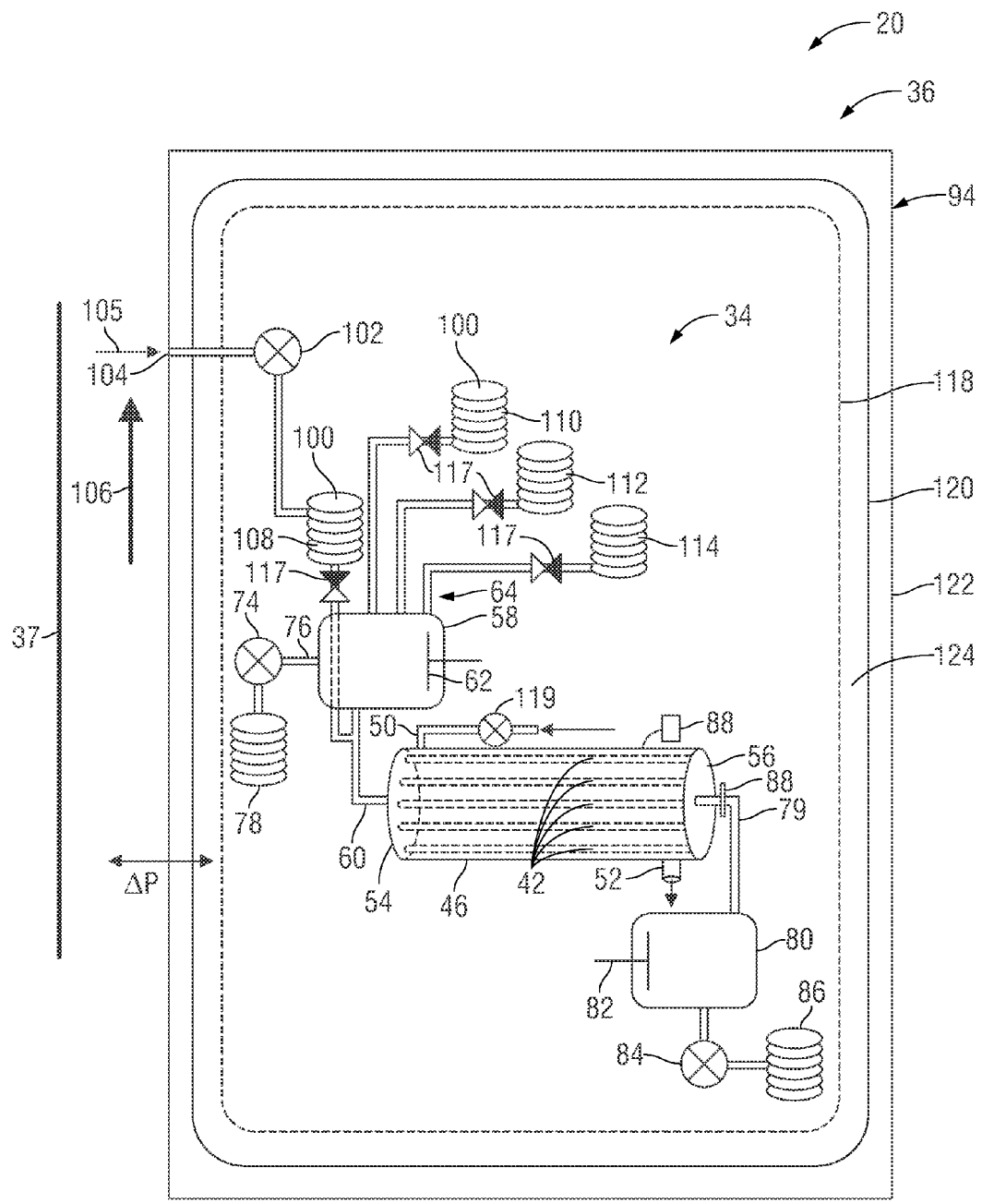
FIG. 5 is a schematic illustration of a capillary electrophoresis system deployed in another example of the enclosed chamber system, according to an embodiment of the disclosure.

Referring generally to FIGS. 4 and 5, embodiments of the capillary electrophoresis system 34 are illustrated as combined with enclosed chamber system 36 that serves as a containment unit which, if desired, can be used to re-create reservoir conditions such that testing of the reservoir sample can be performed under reservoir conditions at the surface location. For example, the enclosed chamber system 36 may be used to create high pressure and/or high temperature environments, via controller 37, similar to those which occur naturally in the subterranean reservoir or other subterranean location. By way of example, enclosed chamber system 36 may comprise an enclosed chamber system 94, such as a pressure controlled chamber system, enclosing the capillary electrophoresis system 34 in whole or in part. In the examples illustrated in FIGS. 4 and 5, the enclosed chamber system 94 comprises a high pressure chamber 96 which encloses the components of capillary electrophoresis system 34 to enable performance of testing operations under subterranean conditions, e.g. reservoir conditions. In at least some applications, the capillary electrophoresis pressure within high pressure chamber 96 may be set slightly higher than the reservoir pressure using, for example, an inert gas 98 such as a noble gas or nitrogen. The higher pressure mitigates the depletion of gases from the reservoir fluid sample tested via fluid testing system 20.

The enclosed chamber system 94 may have several types of constructions designed to maintain the pressure and/or temperature at a desired level and uniformity with respect to the capillary electrophoresis system 34. This also allows the enclosed chamber system 94 to be used in re-creating certain reservoir conditions to enhance the reservoir sample analysis. In the embodiment illustrated in FIG. 4, the enclosed chamber system 94 comprises high pressure chamber 96 enclosing the components of capillary electrophoresis system 34. For example, high pressure chamber 96 may be designed to enclose the components of a capillary electrophoresis system 34 as illustrated and described in the embodiments of FIGS. 2 and 3. However, high pressure chamber 96 also may enclose other components, such as a sample pump 102 coupled with a port 104 exposed to a fluid to be sampled as indicated by arrow 105. For example, port 104 may be positioned in a flow stream 106, e.g. a reservoir flow stream from which reservoir fluids may be sampled. The sample pump 102 delivers the sample to a sample reservoir/vial 108 which, in turn, delivers the sample to flow passage 60. Additionally, high pressure chamber 96 may enclose vials 110, 112, and 114 containing, for example, buffer fluid, rinse fluid, and capillary electrophoresis grade water, respectively. Similarly, high pressure chamber 96 may enclose a coolant reservoir/vial 116 coupled with inlet 50.

In the embodiment illustrated in FIG. 4, high pressure chamber 96 maintains uniform pressure on capillary electrophoresis system 34 at a predetermined pressure level. Hydrophobic membranes 100 on vials 108 and 110 allow gases into the system to maintain pressure in the vials. In operation, a liquid sample is collected via port 104 and pumped to sample reservoir 108 via pump 102 while the capillary electrophoresis system 34 is maintained at uniform pressure by controller 37. Pump 102 enables collection of the sample from a flow stream, such as reservoir flow stream 106. In some applications, the fluid sample is cleaned before delivery to capillaries 42 for analysis. In the illustrated embodiment, the various fluid vials 110, 112, 114 are connected to the inlet vial/anodic chamber 58 and flow from the vials to the anodic chamber 58 is controlled by a plurality of valves 117. Instead of the vials or in conjunction with the vials, piston-operated vessels or combinations of other fluid dispensing methodologies may be combined with the individual vials. Upon opening of a desired valve 117, pump 74 draws the desired fluid into the anodic chamber 58. The fluids flow from anodic chamber 58 and through the desired capillary or capillaries 42 under the influence of an electric field and/or with the assistance of pump 84.

During extended time periods, some depletion of dissolved gas from the fluid sample may occur. However, various adjustments may be made to the methodology to reduce this compositional change. For example, the fluid sample, e.g. reservoir sample, may be pressure equilibrated with the inert gas 98 in the high pressure chamber 96. The equilibration may be achieved via a long diffusion path unit, e.g. a long capillary tube or a column filled with inert fibers or porous materials, so the chemical equilibration is hindered while the pressure equilibration is ensured. In another example, the inert gas 98 may be pre-equilibrated (in a chemical sense) with the sampled fluid.

Referring generally to FIG. 5, another embodiment of enclosed chamber system 36 is illustrated. In this embodiment, enclosed chamber system 36 comprises enclosed chamber system 94 having an impound region 118. Impound region 118 is enclosed by a bellows container 120 which, in turn, is enclosed by a solid container 122. Additionally, the vials 108, 110, 112, 114 may be formed as bellows chambers or vials. Similarly, the waste chambers 78, 86 may be formed as bellows chambers or vials.

The bellows container 120, as well as the various bellows vials/chambers, can be squeezed in or pushed out to maintain the designated pressure on the capillary electrophoresis system 34. In this embodiment, the capillary electrophoresis system 34 may be enclosed, e.g. caged, within impound region 118 which is positioned within bellows container 120. Additionally, the bellows container 120 may be filled with a coolant 124, e.g. a coolant solution, designed to maintain the capillary temperature while also maintaining uniform pressure on capillary electrophoresis system 34.

In an operational example, the fluid testing system 20 is employed in analyzing a fluid sample obtained from a subterranean location, e.g. a wellbore location. Once the capillary electrophoresis system 34 is initialized, coolant is forced through tubing 46 along capillaries 42 by pump 119. After a desired capillary temperature is reached, a designated capillary 42 is prepared for measurement by performing capillary conditioning. During the capillary conditioning, various conditioning procedures may be conducted with respect to the capillary 42. For example, the capillary 42 may be rinsed with buffer fluid, rinse fluid, and capillary electrophoresis grade water from the vials 110, 112 and 114, respectively. In some applications, the capillaries 42 may be coated with an anionic or cationic surfactant. For example, internal coating 44 may comprise the anionic or cationic surfactant. Subsequently, a designated amount of fluid sample is forced into the designated capillary 42 and the sample is followed by injection of a water cap. The inlet reservoir, e.g. inlet vial 58, may be filled with buffer fluid.

Voltage is then applied across the capillary 42 to cause electrochemical separation of the ions. Under the influence of the electric field established by the voltage, ions separate based on their charge and their size. Cations followed by neutrals and anions move towards the cathode 82. (It should be noted that the voltage may be supplied from various power sources, such as a surface power source or a battery located in enclosed chamber system 36.) As the ions move toward the outlet end of the capillary 42, those ions are captured and analyzed by detector system 88. During this fluid sample testing procedure, the temperature may be controlled via coolant 48. Additionally, the pressure acting on capillary electrophoresis system 34 may be balanced to equilibrium or to a desired small pressure differential with respect to the surrounding pressure, e.g. reservoir pressure. Consequently, the accuracy and usefulness of the test data sent to data acquisition and control system 38 is substantially increased.

The design and operation of fluid testing system 20 effectively enables reservoir fluid analysis under selected subterranean conditions and with a variety of analytical techniques in a single system. The capillary electrophoresis system 34 is combined with enclosed chamber system 94 for operation under desired conditions, e.g. reservoir conditions of high temperature and/or high pressure. The fluid testing system 20 provides efficient pressure and thermal control under reservoir conditions which, in turn, improves the reproducibility and reliability of the measurements.

The capillaries 42 may be constructed as narrow bore capillaries able to dissipate heat efficiently. Additionally, a multichannel arrangement utilizing a plurality of capillaries 42 enables the running of multiple measurements in a single operation. Constructing the capillaries 42 as flexible capillaries also provides additional ruggedness to the entire fluid sampling system 20. The use of enclosed chamber system 94 enables analysis of reservoir fluids and other subterranean fluids under re-created conditions which limit or prevent undesirable effects on the fluid sample, e.g. undesirable compositional changes of the fluid sample due to phase separation, scaling, deposition, or the occurrence of other detrimental events.

Figure 6:
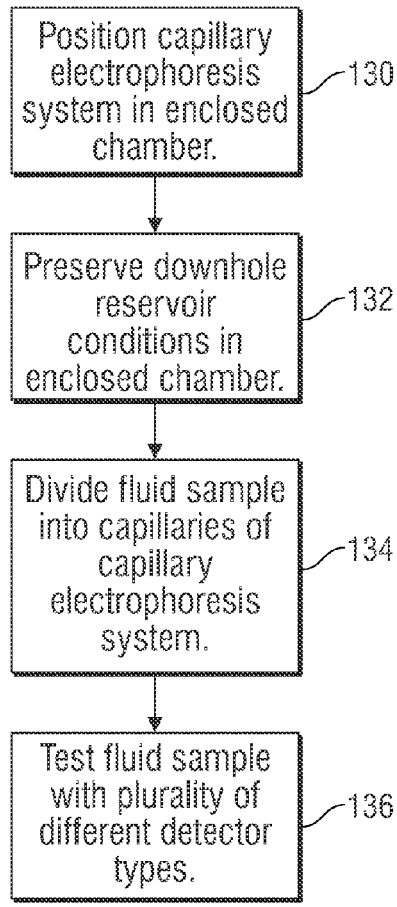
FIG. 6 is a flowchart illustrating an example of a methodology for testing the reservoir sample, according to an embodiment of the disclosure.

Referring generally to FIG. 6, a flowchart is provided to illustrate an example of a fluid testing methodology that may be performed by the capillary electrophoresis system 34 in conjunction with enclosed chamber system 94. In this example, the capillary electrophoresis system 34 is positioned in a containment unit, such as enclosed chamber system 94, as indicated by block 130. The enclosed chamber system 94 enables preservation, e.g. re-creation, of downhole reservoir conditions to facilitate testing, as indicated by block 132. Additionally, the fluid sample is divided into multiple capillaries 42 of the capillary electrophoresis system 34 to enable collection of a variety of data with respect to the fluid sample, as indicated by block 134. The fluid sample may be tested with a plurality of different detector types, as indicated by block 136, to facilitate collection of a variety of data types from a single capillary electrophoresis system 34. Testing of the fluid sample may be carried out at a wellsite surface location or at another suitable location to which the fluid sample may be delivered in a timely manner.

Figure 7:
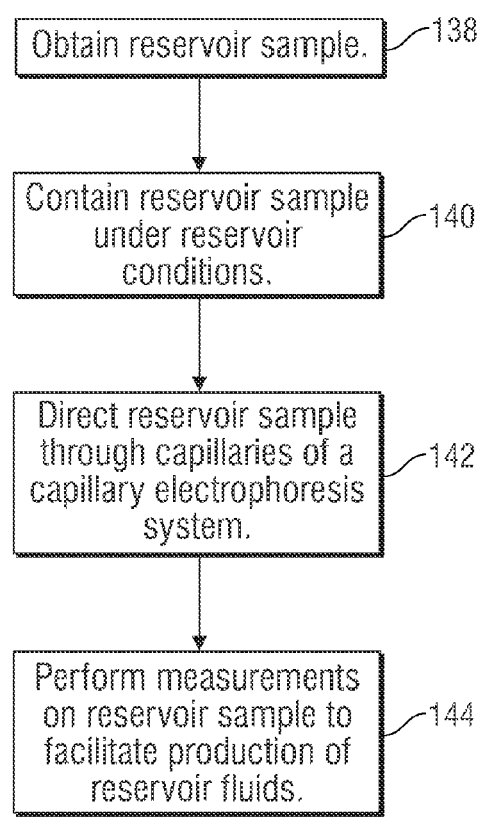
FIG. 7 is a flowchart illustrating another example of a methodology for testing the reservoir sample, according to an embodiment of the disclosure.

Another example of a similar fluid testing methodology is illustrated by the flowchart of FIG. 7. In this example, a reservoir sample of fluid is initially obtained for testing, as indicated by block 138. The reservoir sample is then contained within a testing system under desired reservoir conditions, as indicated by block 140. In certain applications, the reservoir sample is divided into portions and directed through parallel capillaries 42 of capillary electrophoresis system 34, as indicated by block 142. This allows the capillary electrophoresis system 34 to perform a variety of measurements on the reservoir sample designed to increase knowledge of the reservoir and to facilitate production of reservoir fluids, as indicated by block 144.

Depending on the environmental conditions and on the parameters of a given sample testing operation, the overall fluid testing system may utilize a variety of components and component configurations. For example, the enclosed chamber system may employ a variety of membranes, bellows containers, and/or other types of enclosures formed of a variety of materials. Similarly, the capillary electrophoresis system may utilize a variety of pumps, vials, chambers, electrodes, coolants, capillaries, and/or other components arranged in various numbers and configurations. The bellows vials may include a variety of bellows materials and structures. The fluid testing system may be employed to facilitate testing of fluid samples taken from well-related reservoirs, subterranean caverns, subterranean flow networks, and various other subterranean environments. Additionally, the fluid testing system and methodology may be used in other applications in which high pressure and/or high temperature environments may be created/contained in a controlled environment to avoid detrimental changes to the fluid sample prior to completion of the testing.

Although only a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A method for testing a reservoir fluid sample, comprising:
   providing a capillary electrophoresis system that includes i) a plurality of capillaries and corresponding plurality of detectors, wherein the plurality of capillaries has an inlet side opposite an outlet side, ii) a first chamber having an anode, wherein the first chamber is fluidly coupled to the inlet side of the plurality of capillaries, and iii) a second chamber having a cathode, wherein the second chamber is fluidly coupled to the outlet side of the plurality of capillaries;
   obtaining the reservoir fluid sample; and
   directing the reservoir fluid sample from the first chamber through the plurality of capillaries for supply to the second chamber and applying a voltage across the anode and the cathode to cause electrochemical separation of constituent elements with respect to the reservoir fluid sample and migration of the constituent elements through the plurality of capillaries, wherein the plurality of detectors are configured to perform different measurement tests on the constituent elements that migrate through the plurality of capillaries to obtain measurements of parameters with respect to the reservoir fluid sample;
   wherein at least the plurality of capillaries, the corresponding plurality of detectors, the first chamber and the second chamber of the capillary electrophoresis system are enclosed in a chamber that is maintained at a controlled pressure by an external controller during the directing and the measurement tests performed by the plurality of detectors.

2. The method as recited in claim 1, further comprising balancing a relatively high pressure of the chamber with an internal pressure of the capillary electrophoresis system until achieving a desired pressure differential.

3. The method as recited in claim 2, wherein balancing a relatively high pressure of the chamber with an internal pressure of the capillary electrophoresis system comprises setting the internal pressure slightly higher than the relatively high pressure.

4. The method as recited in claim 1, further comprising flowing a coolant along a capillary of the capillary electrophoresis system until the capillary is at a desired temperature.

5. The method as recited in claim 1, further comprising covering a plurality of vials of the capillary electrophoresis system with a hydrophobic membrane.

6. The method as recited in claim 1, further comprising forming a plurality of vials of the capillary electrophoresis system as bellows containers.

7. The method as recited in claim 1, wherein the plurality of capillaries are disposed inside a microchip channel device.

8. The method as recited in claim 1, further comprising using piston-operated vessels to deliver the reservoir fluid sample to the plurality of capillaries.

9. The method as recited in claim 4, wherein flowing a coolant along a capillary of the capillary electrophoresis system comprises flowing the coolant through a tube surrounding the capillary.

10. The method as recited in claim 4, wherein flowing a coolant along a capillary of the capillary electrophoresis system comprises flowing the coolant through a tube along the plurality of capillaries.

11. The method as recited in claim 1, further comprising performing capillary conditioning on a particular capillary prior to introducing the reservoir fluid sample into the particular capillary.

12. The method as recited in claim 1, wherein the plurality of capillaries have an internal coating.

13. The method as recited in claim 1, wherein:
   the plurality of detectors are disposed within tubing on the exterior of the plurality of capillaries.

14. The method as recited in claim 1, wherein the capillary electrophoresis system further includes at least one test fluid reservoir in fluid communication with the plurality of capillaries, wherein the at least one test fluid reservoir is enclosed in the chamber that is maintained at the controlled pressure by the external controller during the directing and the measurement tests performed by the plurality of detectors.

15. The method as recited in claim 14, wherein the at least one test fluid reservoir contains test fluids selected from the group consisting of rinse solution, solvent, separation buffer, high purity water.

16. The method as recited in claim 14, further comprising coating certain capillaries with an internal coating.

17. The method as recited in claim 1, wherein the capillary electrophoresis system includes tubes that surround the plurality of capillaries, wherein the tubes contain fluid that protects the plurality of capillaries against physical shocks.

18. The method as recited in claim 17, wherein the fluid comprises a coolant that controls temperature of the plurality of capillaries.

19. The method as recited in claim 1, wherein the measurement tests performed by the plurality of detectors are based on at least one spectroscopic technique that involve emission or absorption of an optical or other electromagnetic signal.

20. The method as recited in claim 1, wherein the measurement tests performed by the plurality of detectors are based on at least one electrochemical technique involving conductivity or resistance or potentiometry.

21. The method as recited in claim 1, wherein the constituent elements comprise ions and/or molecules that undergo electrochemical separation and migration through the plurality of capillaries.

22. The method as recited in claim 1, wherein the constituent elements comprise ions that undergo electrochemical separation and migration through the plurality of capillaries, and the measurement tests performed by the plurality of detectors detect cations followed by neutrals and anions in the reservoir fluid sample.

23. The method as recited in claim 1, wherein the controlled pressure is configured to simulate downhole reservoir conditions.

24. The method as recited in claim 1, wherein the plurality of capillaries are flexible capillaries.

25. The method as recited in claim 1, wherein the plurality of capillaries are silica capillaries.

* * * * *